United States Patent [19]

Perrut et al.

[11] 4,362,046
[45] Dec. 7, 1982

[54] LIQUID SAMPLE INJECTION SYSTEM FOR GAS CHROMATOGRAPHY

[75] Inventors: Michel Perrut, St Nicolas de Port; Marcel Pointet, Serezin du Rhone; Henri T. de Santerre, Saint Nazaire, all of France

[73] Assignee: Societe Nationale Elf Aquitaine, Paris, France

[21] Appl. No.: 140,114

[22] Filed: Apr. 14, 1980

[30] Foreign Application Priority Data

Apr. 26, 1979 [FR] France ............................... 79 10649

[51] Int. Cl.³ .............................................. G01N 31/08
[52] U.S. Cl. ................................................... 73/23.1
[58] Field of Search .............. 73/23.1, 863.71, 863.72, 73/863.73; 23/232 C; 422/89

[56] References Cited

U.S. PATENT DOCUMENTS

| 3,236,092 | 2/1966 | Carter | 73/23.1 |
|---|---|---|---|
| 3,372,573 | 3/1968 | Sanford et al. | 73/23.1 |
| 3,394,582 | 7/1968 | Munro et al. | 73/23.1 |
| 4,007,626 | 2/1977 | Roof et al. | 73/23.1 |
| 4,024,752 | 5/1977 | Orlando | 73/23.1 |
| 4,057,997 | 11/1977 | Chandler | 73/23.1 |

FOREIGN PATENT DOCUMENTS 2227890 11/1974 France ................................ 73/23.1

*Primary Examiner*—Stephen A. Kreitman
*Attorney, Agent, or Firm*—Burgess, Ryan and Wayne

[57] ABSTRACT

An improvement in the method of injection of liquid into an industrial device for separation by gas chromatography by means of a vaporizer swept by a vector, the liquid being brought to the vaporizer by a pipe containing a valve which, when opened and closed, permits the injection at a given rate of flow, of the predetermined quantity of liquid, the rapid purge of the fluids contained in the vaporizer and the adjacent ducts at the end of the injection, and the continuous slow purge between injections being insured by a system of valves, wherein the instantaneous vaporization is insured by a vaporizer-exchanger, and a branch permits the vector gas to short-circuit the vaporizer when the injection is shut off, while feeding the column.

3 Claims, 5 Drawing Figures

LIQUID SAMPLE INJECTION SYSTEM FOR GAS CHROMATOGRAPHY

BACKGROUND OF THE INVENTION

The present invention relates to an improvement in a device for injection of liquid loads into an industrial system of gas chromatography, involving large diameter columns.

As already set forth in French Pat. No. 2,227,890, assigned to the same assignee of the instant application, the injection of the liquid load, into a gas chromatography separation device, constitutes an important element in the obtaining of a good separation in the chromatographic column. As a matter of fact, the highest efficiency is obtained when the curve of fluctuation of the concentration of the injected product, as a function of the time, exhibits a rectangular form for the injection time and the time of a cycle, as can be seen in FIG. 1 in the attached drawing. In this figure, the times are plotted in the abscissa and the concentrations of the product injected into the vector gas is plotted in the ordinate.

The embodiment of an injection of this type, prevents the passage into the column, before or after the injection, of trails of the mixture to be separated, which would upset the equilibrium inside the column between the phases present, and would lead to a poor resolution of the mixture to be separated.

In classic fashion, the liquid is introduced into a vaporizer and the gas which is produced is transported into the column by the motive force of the vector gas. The start of the injection is controlled by the opening of a valve placed in the piping that feeds the liquid to the vaporizer, and the end of the injection by the closing of this same valve. This technique leads to injections of non-rectangular form, with a trail due to the vaporization of small quantities of the product to be separated remaining in the vaporizer after the injection is stopped. Thus, there is described in the aforesaid French patent, a method and device for injection of liquid into a gas chromatography column with a vaporizer continuously swept by a vector gas, the liquid being brought to the vaporizer by a pipe equiped with a valve which is opened and then closed to permit the injection at a given rate of flow, of the desired quantity of liquid to be injected, a fast purge being made at the end of the injection in the pipe between the valve and the vaporizer, as well as a continuous purge at a very low rate of flow between the injection periods.

This device, used for columns 125 mm in diameter, is represented by the schematic in FIG. 2; the preheated vector gas is introduced at 8 and continuously sweeps the vaporizer-exchanger 6 before entering the chromatographic column 9 where it is distributed through a fritted plate 10; the liquid product to be processed is introduced at 3.

During the injection, valve 3 is opened and fast-purge valve 2 closed; the liquid is then vaporized very rapidly in the presence of the vector gas in exchanger 6. To improve the form of the injection "crenellations" valve 2 is opened for a few seconds, immediately after the end of the injection in order to sweep the portion of line comprised between vaporizer 6 and valve 3 and then filled with product to be processed. The manual microvalve 1 allows continuous passage of a very small flow in order to palliate a slight leakage of remote-controlled injection valve 3.

It has been found that this device has the following drawbacks:
constant overheating of the vector gas between the periods of injection of the mixture to be vaporized and separated,
"Trailing" of injection crenellations inducing less separation in the column, particularly for large-dimensioned vaporizers (column with a diameter of 400 mm and more),
Risk of overheating and cracking of small quantities of products to be separated—which are, generally speaking, thermally fragile products—inducing a clogging of the fritted input piece in the column, and a gradual coking of the sides of the vaporizer; these cases of stoppage calling for long cleaning periods that seriously affect the economy of the method.

SUMMARY OF THE INVENTION

To remedy these drawbacks, the instnt invention is directed to a new pattern of fluid flows in the vaporizer that is particularly applicable to the devices necessary for large-diameter columns on the order of 400 mm and more.

According to the invention, the injection of liquid into the industrial device for separation by gas chromatography is operated by means of a vaporizer swept by a vector gas, the liquid being brought to the vaporizer through a pipe having a valve which, when opened and closed, permits the injection at a given rate of flow of a predetermined quantity of liquid, the fast purge of the fluids contained in the vaporizer and the adjacent ducts at the end of the injection, the continuous, slow purge between injections being insured by a system of valves, characterized in that the instantaneous vaporization is insured by a vaporizer-exchanger, and that a branch enables the gas to short-circuit the vaporizer when the injection is shut off, while feeding the column.

IN THE DRAWINGS

DETAILED DESCRIPTION

Figure 3:
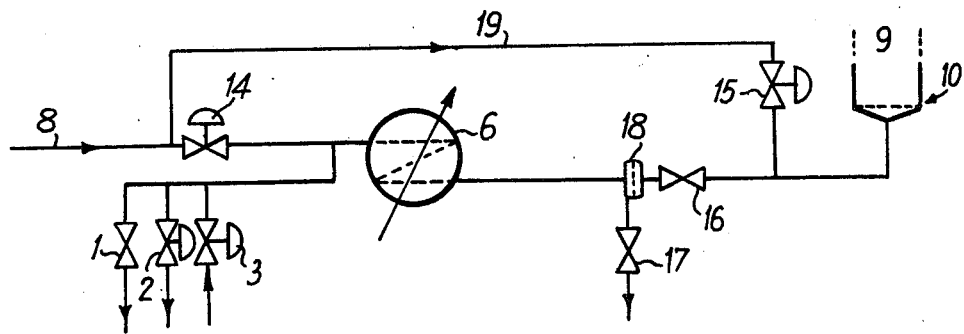
FIG. 3 is a schematic view of an injection device according to the present invention, said device being used to inject vaporized liquid loads in a chromatographic column.

The hookup is illustrated in FIG. 3, in which 9 represents the chromatographic column, 6 the exchanger-vaporizer fed by a heat-bearing fluid, 1 a manual purge valve with a very low output, open during the normal operation of the installation, 2 a remote-controlled purge valve with higher output, 3 a remote-controlled admission valve for the liquid to be treated, 14 and 15 are remote-controlled valves in the vector gas circuit, 16 and 17 are manual valves that are, respectively, open and closed in the normal operation of the installation.

During the period of injection of the products to be separated, valves 3 and 14 are opened, valves 2 and 15 closed; the preheated hydrogen introduced at 8 and the liquid to be vaporized pass through the exchanger, and the vaporization is produced quasi-instantaneously.

Outside of the injection period, valves 3 and 14 are closed, valve 15 is open, the preheated hydrogen then short-circuits the vaporizer and arrives directly at the column head without overheating; for a few seconds immediately after the end of the injection, valve 2 is opened, which permits purging the entire vaporization circuit of the hydrogen mixture—the slow purge valve 1 has the same function as in the earlier device described above.

It will be easy to understand that this fluid circulation device avoids the overheating of the vector gas outside the periods of injection, since it then takes branch 19, and the injection crenellations are perfectly rectangular, due to the use of the fast purge which evacuates all of the contents of the exchanger and of the adjacent lines. The result is an overall efficiency of separation which is definitely better than with the earlier device as shown by the example below.

Furthermore, a filtration device 18 has been included between the exchanger and the column, which makes it possible to stop any particle that could clog the fritted piece 10 at the entrance to the column.

In addition, the cleaning of the exchanger, or the changing of the filter 18 or any other liquid injection part or line, can be operated without completely shutting down the installation, since the vector gas takes the branch 19 and the valves 14 and 16 isolates the assembly of exchanger, fritted piece and adjacent lines. This avoids having to cool, then reheat the column, a long procedure, harmful both to the quality of the column and to the economy of the method. Moreover, the manual valve 17 can be used for periodic drainage of the vessel containing the filter element.

EXAMPLE 1

Using an industrial chromatography apparatus equipped with a column of 125 mm and a plate exchanger fed by heat-bearing fluid to operate the vaporization, injections of linalool are made under the following conditions:

flow of vector gas (hydrogen) at 180°:17.5m$^3$/h
flow of linalool: 207 moles/hr. or 8.7 g/sec.

Figure 1:
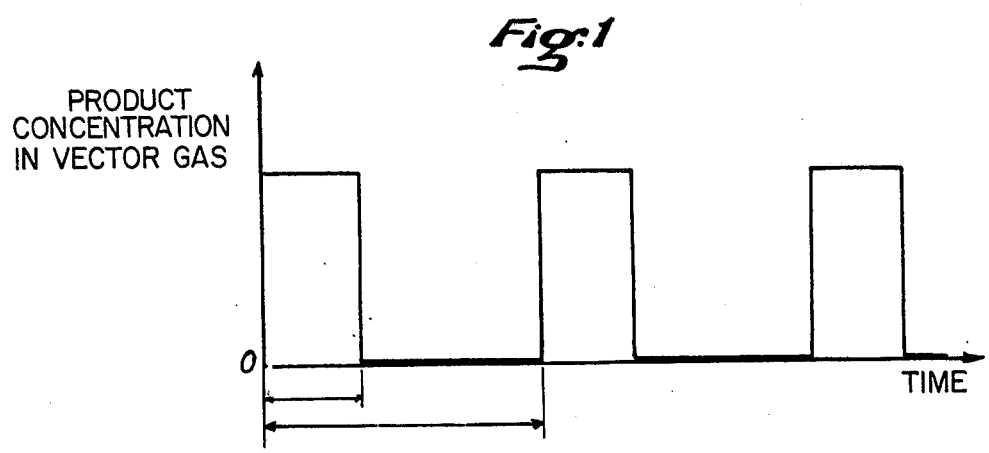
FIG. 1 is a curve of the concentration of the product in the vector gas.
Figure 2:
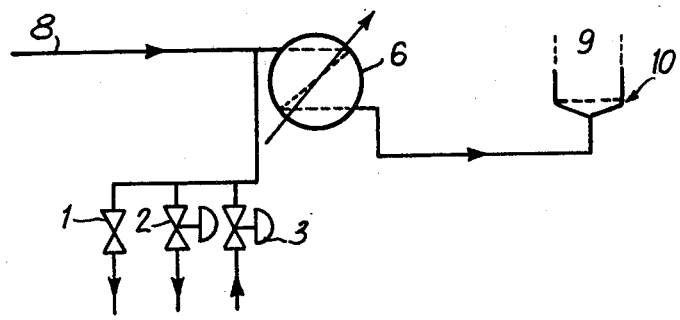
FIG. 2 is a schematic view of an injection device according to the prior art.

The flow of heat-bearing fluid in the exchanger is 2m$^3$/hour, approximately, and its temperature, 210° C. The temperature is 180° C. Curves 4 and 5 represent, respectively, the recordings of the peaks without a by-pass system (hookup in FIG. 2) and with by-pass system (hookup in FIG. 3).

Figure 4:
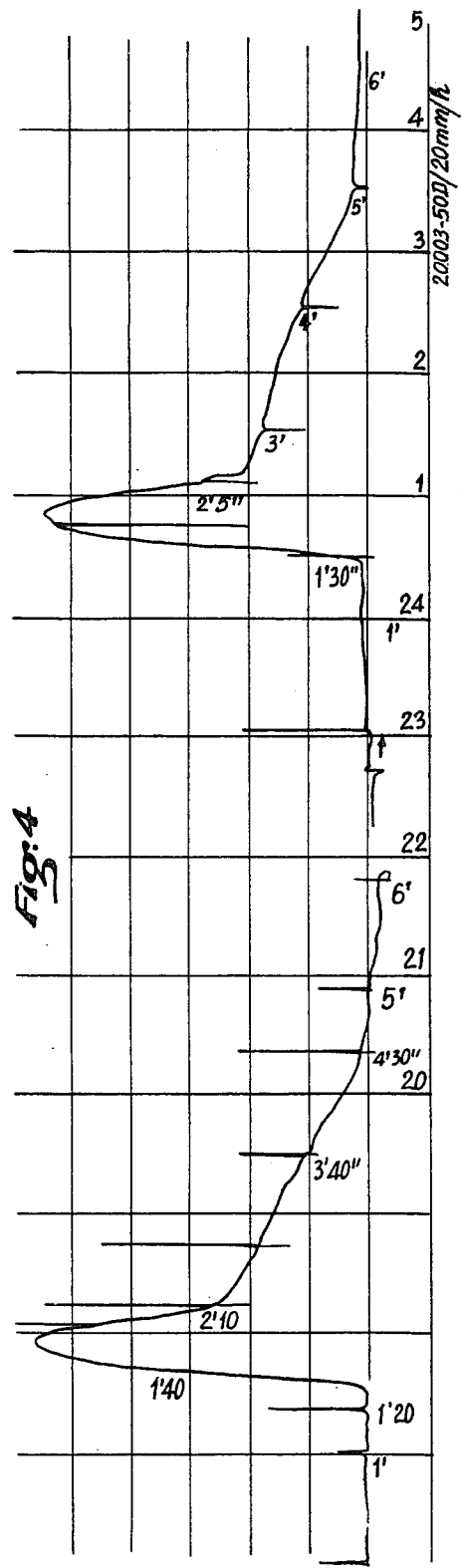
FIG. 4 is a chromatographic recording of peaks without a by-pass system (hookup in FIG. 2)
Figure 5:
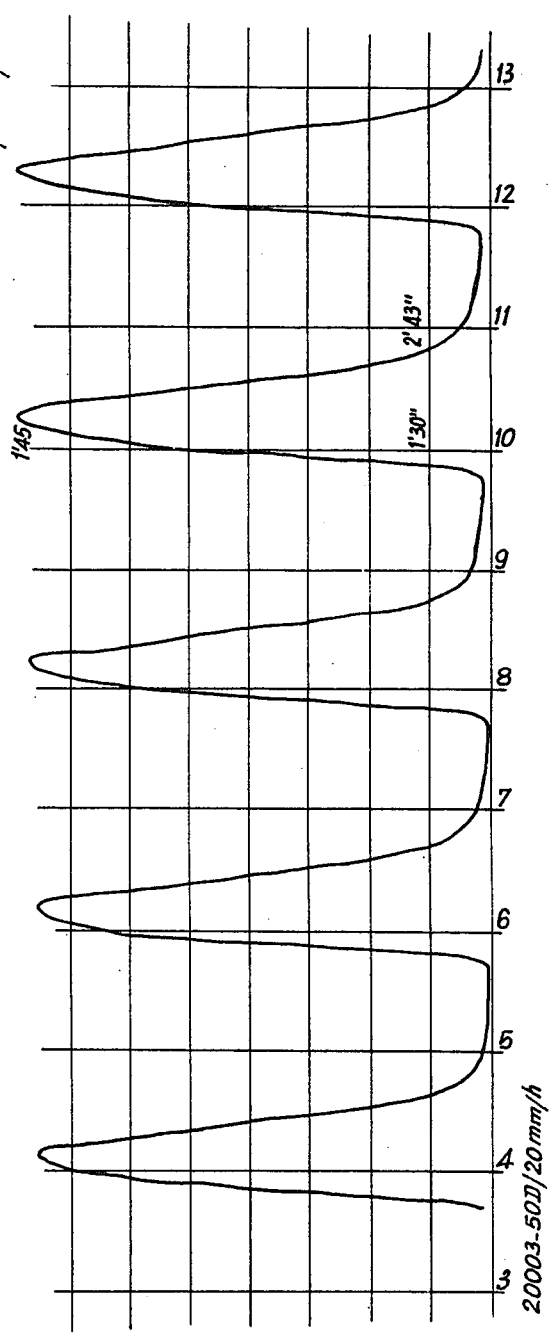
FIG. 5 is a chromatographic recording of peaks with a by-pass system (hookup in FIG. 3).

A very substantial trail is noted on the peaks obtained in the case of the use of the earlier system of injection (FIG. 4), while the peaks obtained with the system of injection constituting the subject of the present invention leads to very narrow peaks, FIG. 5, making for very good productivity in the case of separation of a mixture.

What is claimed is:

1. A system for gas chromatography by feeding a vaporized liquid to be processed to a chromatographic column via a vaporizer swept by a vector gas, said system comprising:

first valve means for coupling a conduit for said vector gas to an inlet of said vaporizer;

means for enabling said vaporizer to substantially instantaneously vaporize said liquid;

sample injection means including a second valve means for intermittently coupling a conduit for said liquid to an inlet of said vaporizer while the vector gas is passing through said vaporizer so that the concentration of said vaporized liquid in said vector gas varies with time with an essentially rectangular waveform;

an outlet conduit for coupling the vaporized liquid and vector gas mixture from said vaporizer to an inlet of said chromatographic column;

a bypass conduit for providing communication between said vector gas conduit and said outlet conduit; and bypass valve means in said bypass conduit for selectively permitting said vector gas to flow directly to said chromatographic column when said vaporizer is inactive.

2. The system according to claim 1, wherein said chromatographic column has a fritted input piece, further comprising a filter element interposed in said outlet conduit for blocking passage of particles which could clog said input piece.

3. The system according to claim 1 or 2, further comprising filter isolation valve means in said outlet conduit for isolating said filter element from said bypass conduit and chromatographic column inlet, to permit cleaning of said filter element without disturbing the flow of vector gas to said column through said bypass conduit.

* * * * *